United States Patent
Bar-El et al.

(10) Patent No.: US 10,926,027 B2
(45) Date of Patent: Feb. 23, 2021

(54) NOISE AND VIBRATION DAMPENING MOUNTING MODULE FOR INJECTOR

(71) Applicant: West Pharma. Services IL, Ltd., Ra'anana (IL)

(72) Inventors: Yossi Bar-El, Beit Arye (IL); Gil Yigal, Gan Yavne (IL); Igor Isakov, Rehovot (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/617,985

(22) PCT Filed: May 29, 2018

(86) PCT No.: PCT/US2018/034882
§ 371 (c)(1),
(2) Date: Nov. 27, 2019

(87) PCT Pub. No.: WO2018/222591
PCT Pub. Date: Dec. 6, 2018

(65) Prior Publication Data
US 2020/0188578 A1 Jun. 18, 2020

Related U.S. Application Data

(60) Provisional application No. 62/512,486, filed on May 30, 2017.

(51) Int. Cl.
*A61M 5/142* (2006.01)
*A61M 5/20* (2006.01)
(Continued)

(52) U.S. Cl.
CPC .......... *A61M 5/14248* (2013.01); *A61M 5/20* (2013.01); *A61M 5/14566* (2013.01);
(Continued)

(58) Field of Classification Search
None
See application file for complete search history.

(56) References Cited

U.S. PATENT DOCUMENTS 5,034,004 A * 7/1991 Crankshaw ......... A61M 5/1452
604/154
6,471,436 B1 10/2002 Gjata et al.
(Continued)

FOREIGN PATENT DOCUMENTS

CN 202086877 U 12/2011
JP 5616906 B2 10/2014

OTHER PUBLICATIONS

Int'l Search Report and Written Opinion dated Aug. 14, 2018 in Int'l Application No. PCT/US2018/034882.
(Continued)

*Primary Examiner* — Nathan R Price
*Assistant Examiner* — Weng Lee
(74) *Attorney, Agent, or Firm* — Panitch Schwarze Belisario & Nadel LLP (57) ABSTRACT

An independent mounting module is receivable within a housing of an injector configured to dispense a substance from a cartridge insertable into the housing through an injection needle of the injector. The mounting module includes a first mount and a second mount. The first mount is configured to receive a driving assembly engageable with the cartridge to expel the substance therefrom. The first mount is selectively securable to the injector housing and has a cantilevered mounting arm extending therefrom. The second mount is configured to receive an actuator operatively connectable with the driving assembly. The second mount is attached to the cantilevered mounting arm and suspended therefrom, thereby being supported by the cantilevered mounting arm.

20 Claims, 5 Drawing Sheets

(51) Int. Cl.
  *A61M 5/145*  (2006.01)
  *A61M 5/315*  (2006.01)
(52) U.S. Cl.
  CPC .............. *A61M 2005/14252* (2013.01); *A61M 2005/31518* (2013.01); *A61M 2005/31588* (2013.01)

(56) References Cited

U.S. PATENT DOCUMENTS

| | | | | |
|---|---|---|---|---|
| 2001/0034502 | A1* | 10/2001 | Moberg | A61M 5/16831 604/154 |
| 2001/0041869 | A1* | 11/2001 | Causey, III | A61M 5/1456 604/152 |
| 2003/0060765 | A1* | 3/2003 | Campbell | G16H 20/17 604/131 |
| 2007/0233003 | A1 | 10/2007 | Radgowski et al. | |
| 2010/0191187 | A1* | 7/2010 | Kim | A61M 5/14244 604/154 |
| 2012/0172817 | A1 | 7/2012 | Bruggemann et al. | |
| 2014/0343406 | A1 | 11/2014 | Damjanovic | |

OTHER PUBLICATIONS

Int'l Preliminary Report of Patentability dated Aug. 16, 2019 in Int'l Application No. PCT/US2018/034882.
Written Opinion of the International Preliminary Examining Authority dated May 9, 2019 in Int'l Application No. PCT/US2018/034882.

* cited by examiner

NOISE AND VIBRATION DAMPENING MOUNTING MODULE FOR INJECTOR

CROSS-REFERENCE TO RELATED APPLICATIONS

This application is a section 371 of International Application No. PCT/US2018/034882, filed May 29, 2018, which was published on Dec. 6, 2018 under International Publication No. WO 2018/222591 A1, and which claims priority from U.S. Provisional Patent Application No. 62/512,486 titled "Noise Dampening Motor Mount For Drug Delivery Device", filed on May 30, 2017, the entire contents of each of which are incorporated by reference herein.

BACKGROUND OF THE DISCLOSURE

The present disclosure is generally directed to a noise and vibration dampening mounting module, and, more particularly, to a noise and vibration dampening mounting module independently securable in a wearable injector.

Wearable injectors are often motor operated. Generally, the motor is mounted within the injector directly to the injector chassis, thereby transferring vibration to the injector chassis and/or creating noise. Such vibration and noise may bother the user wearing the injector or otherwise cause the user anxiety.

One approach to reducing motor vibration and associated noise is to reduce motor speed. Motor speed reduction, however, may adversely restrict the attainable and desired delivery rates of the injector. Another approach to reducing motor vibration and associated noise is to utilize motors constructed of specialized noise and vibration reducing components. Such motors are relatively more costly, however, and utilizing such motors would increase the cost of the injector to the end user.

Therefore, it would be advantageous to manufacture a module for mounting the motor, or other actuator, in the injector housing, that is configured to absorb and dampen vibration and associated noise.

BRIEF SUMMARY OF THE DISCLOSURE

Briefly stated, one aspect of the present disclosure is directed to an independent mounting module receivable within a housing of an injector configured to dispense a substance from a cartridge insertable into the housing through an injection needle of the injector. The mounting module comprises a first mount and a second mount. The first mount is configured to receive a driving assembly engageable with the cartridge to expel the substance therefrom. The first mount is selectively securable to the injector housing and has a cantilevered mounting arm extending therefrom. The second mount is configured to receive an actuator operatively connectable with the driving assembly. The second mount is attached to the cantilevered mounting arm and suspended therefrom, thereby being supported by the cantilevered mounting arm.

Another aspect of the present disclosure is directed to an injector. The injector comprises a housing configured to receive a cartridge therein. An injection needle is fluidly connectable with the cartridge and configured to pierce a skin surface of a subject. An independent mounting module is receivable within the housing and comprises a first mount and a second mount. The first mount is selectively securable within the injector housing, and has a cantilevered mounting arm extending therefrom. The second mount is attached to the cantilevered mounting arm and suspended therefrom, thereby being supported by the cantilevered mounting arm. A driving assembly is mounted in the first mount, the driving assembly being engageable with the cartridge to expel a substance therefrom and through the injection needle. An actuator is mounted in the second mount, the actuator being operatively connected with the driving assembly.

BRIEF DESCRIPTION OF THE DRAWINGS

The following detailed description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the mounting module, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1:
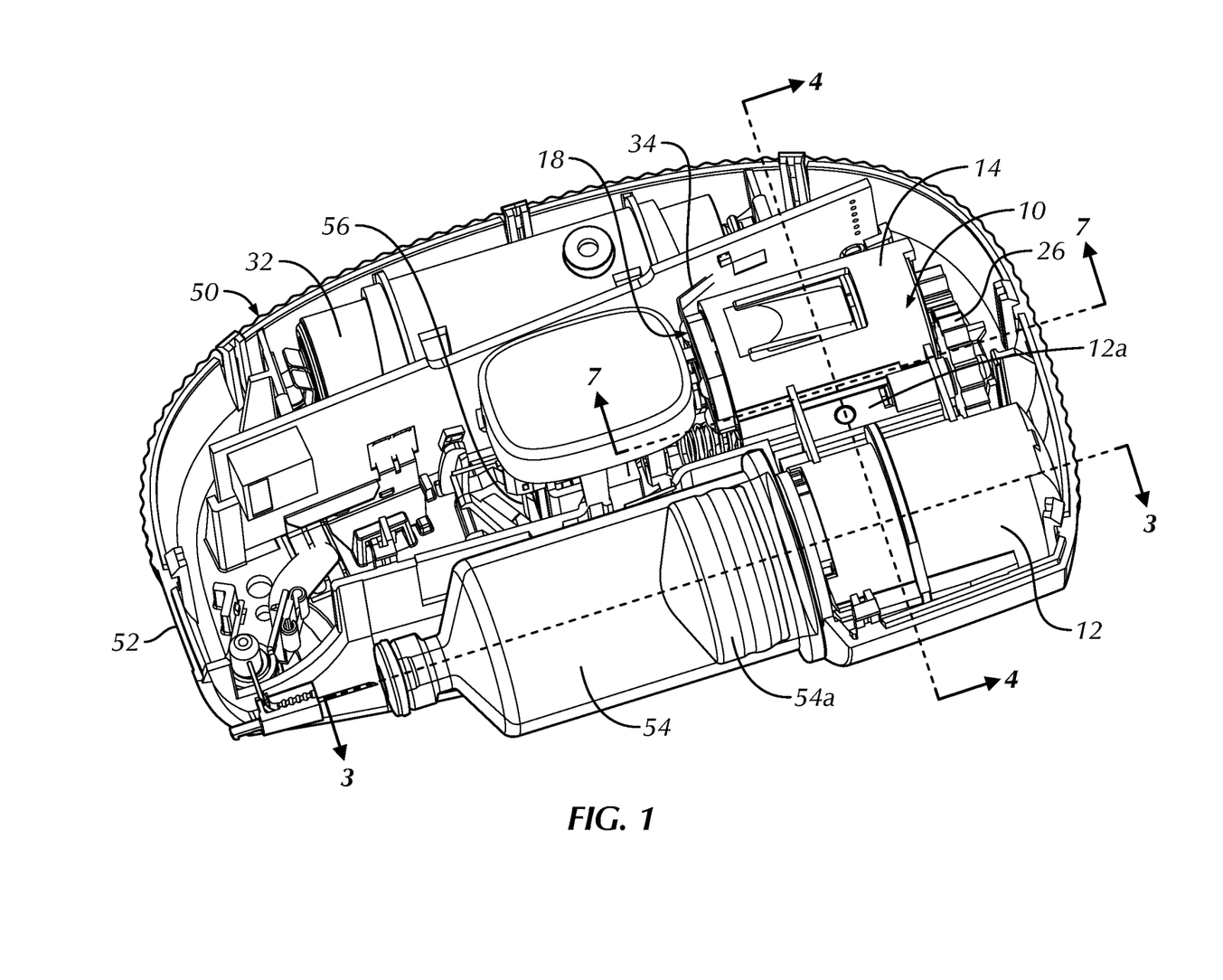
FIG. 1 is a partial perspective view of a wearable injector, having an independent mounting module in accordance with an embodiment of the present disclosure, secured therein.

Referring to the drawings in detail, wherein like numerals indicate like elements throughout, there is shown in FIGS. 1-6 an independent mounting module, generally designated 10, in accordance with an embodiment of the present disclosure. Generally, the independent mounting module 10 is receivable within a housing 52 of a wearable injector (patch injector) 50, such as, for example, without limitation, a wearable drug injector. As should be understood by those of ordinary skill in the art, and as best shown in FIG. 1, a wearable injector 50 generally comprises a housing 52 that houses a cartridge or reservoir 54 containing a substance therein, wherein the cartridge 54 is sealed at one end by a piston 54a. The cartridge 54 is fluidly connectable to an injection needle 56, to dispense the substance within the cartridge 54 through the needle 56 to a user.

Figure 2:
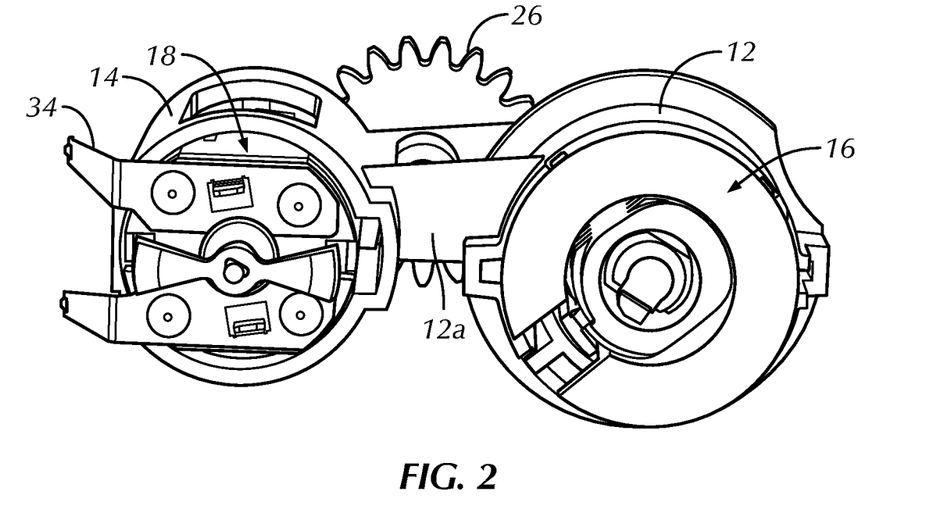
FIG. 2 is a top and front perspective view of the mounting module of FIG. 1.
Figure 6A:
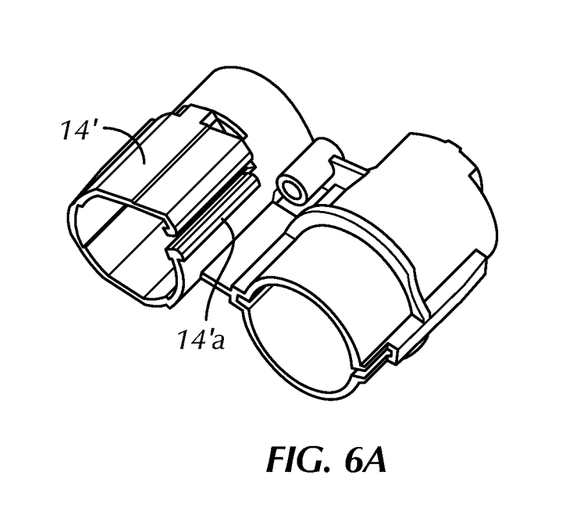
FIG. 6A is a top and front perspective view of an alternative configuration of the mounting module of FIG. 1.
Figure 6B:
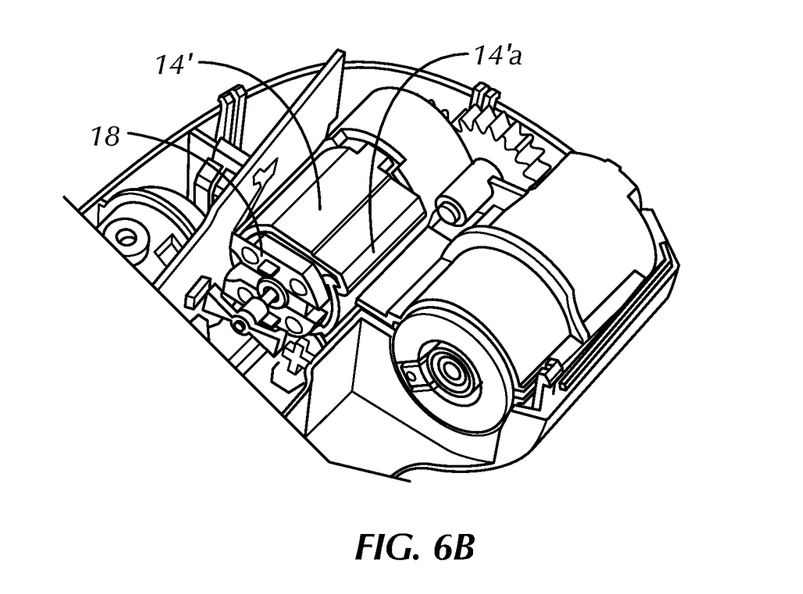
FIG. 6B is a partial perspective view of the wearable injector of FIG. 1, having the mounting module of FIG. 6A secured therein.

Turning to FIG. 2, the mounting module 10 comprises a first mount 12 and a second mount 14. The first mount 12 takes the form of a sleeve to slidably receive and support a driving assembly 16, and the second mount 14 takes the form of another sleeve to slidably receive and support an actuator 18, but the disclosure is not so limited. The first mount 12 generally corresponds in size and shape to the driving assembly 16, and the second mount 14 generally corresponds in size and shape to the actuator 18, and the mounts 12, 14 secure the driving assembly 16 and the actuator 18, respectively, via snap connections. As should be understood by those of ordinary skill in the art, however, the first mount 12 and the second mount 14 may receive and secure the driving assembly 16 and the actuator 18, respectively, via alternative means currently known or that later become known. As one example, without limitation, and as shown in FIGS. 6A and 6B, at least one of the mounts 12', 14' (14' in FIGS. 6A, 6B) may be selectively manipulatable from a radially expanded configuration (FIG. 6A) to a radially contracted configuration (FIG. 6B). As shown, the sidewall of the second mount 14' may include an engageable and disengageable connection 14'a, e.g., a snap connection, wherein, when disengaged, the second mount 14' is radially expanded to receive the actuator 18 therein. Afterwards, the connection 14'a in the sidewall of the mount 14' is engaged, placing the mount 14' into the radially contracted configuration and securing the actuator 18. The same structural features may be applied to the first mount 12.

In the illustrated embodiment, the driving assembly 16 takes the form of a telescopic driving assembly, but the disclosure is not so limited. The driving assembly 16 is configured to engage and advance the piston 54a through the cartridge 54 to expel the substance out of the cartridge 54. One example of a driving assembly 16 is described in U.S. patent application Ser. No. 14/725,009, entitled "Linear Rotation Stabilizer For A Telescoping Syringe Stopper Driverdriving Assembly", the entire contents of which are incorporated by reference herein.

Figure 3:
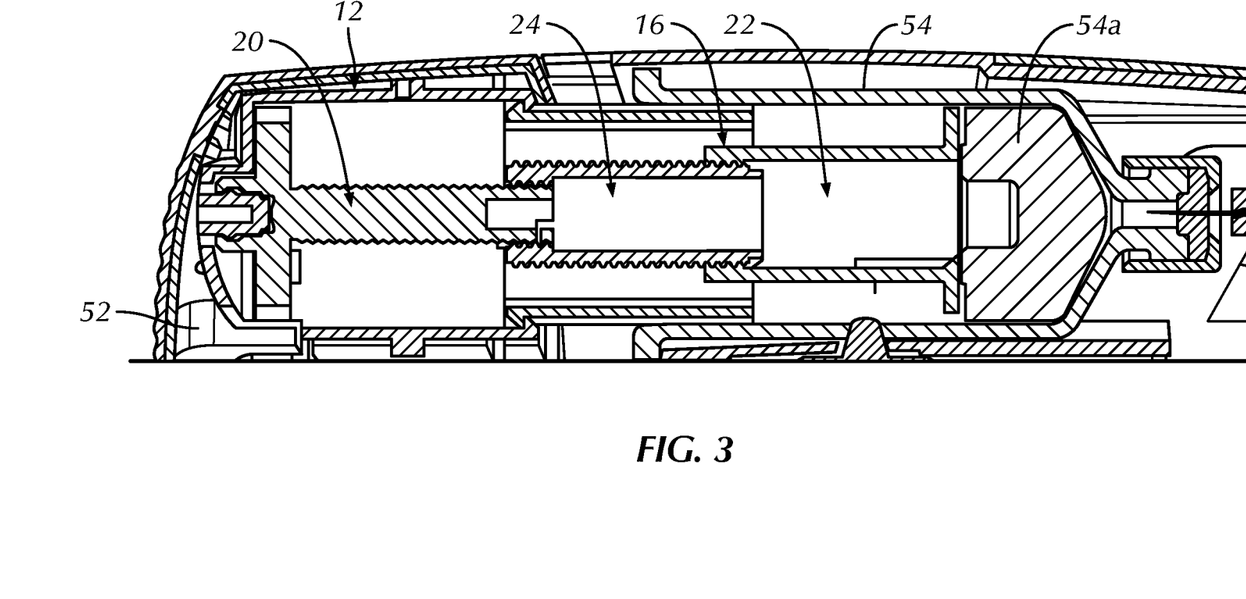
FIG. 3 is a partial cross-sectional view of the mounting module of FIG. 1, taken along the sectional line 3-3 of FIG. 1, with an extended driving assembly mounted thereto.

In the illustrated embodiment, and as shown best in FIG. 3, the driving assembly 16 includes a first shaft 20 and a second shaft 22 telescopically connected with the first shaft 20 and axially movable relative to the first shaft 20. Rotation of the first shaft 20 axially drives the second shaft 22 from a retracted configuration (FIGS. 1, 2) to an extended configuration (FIG. 3) to engage and advance the piston 54a through the cartridge 54. In the illustrated embodiment, as shown best in FIG. 3, an optional third shaft 24 is threadedly connected to the first shaft 20 and threadedly connected to the second shaft 22, connecting the first shaft 20 with the second shaft 22. Thus, rotation of the first shaft 20 rotates and axially drives the third shaft 24, which, in turn, axially drives the second shaft 22. The second shaft 22 is, therefore, axially movable relative to the first shaft 20 and the third shaft 24. Accordingly, the first, third and second shafts 20, 24, 22 form an axially telescoping assembly.

Turning to the actuator 18 (see FIGS. 1, 2, 5), the actuator 18 takes the form of a motor in the illustrated embodiment, but the disclosure is not so limited. For example, the actuator 18 may take the form of a spring actuator, a gaseous actuator, a chemical actuator, an electrical actuator, an electromechanical actuator, combinations thereof, or the like. The actuator 18 drives expansion of the driving assembly 16 and is operatively connected to the driving assembly 16 via a transmission gear 26.

The first mount 12 includes a cantilevered mounting arm 12a extending therefrom, and the second mount 14 is attached to the cantilevered mounting arm 12a and suspended therefrom. The fulcrum of the cantilevered mounting arm 12a is at the interface between the mounting arm 12a and the first mount 12. In the illustrated embodiment, the cantilevered mounting arm 12a extends substantially laterally from the first mount 12 and generally parallel with an underside of the injector housing 52, but the disclosure is not so limited. In the illustrated embodiment, the transmission gear 26 is secured to the independent mounting module 10 via mounting to the cantilevered mounting arm 12a (but the disclosure is not so limited), and is positioned to operatively connect the actuator 18 with the driving assembly 16. For example, as shown in FIG. 1, the mounting arm 12a defines a sleeve therein to receive a shaft of the transmission gear 26 to position the transmission gear 26 in connection, e.g., meshed with, with the actuator 18 and the driving assembly 16. Alternatively, the transmission gear 26 may be mounted to the first mount 12, the second mount 14 or elsewhere on the mounting module 10 wherein the transmission gear 26 operatively connects the actuator 18 with the driving assembly 16.

The mounting module 10, configured to support the driving assembly 16, the actuator 18 and the transmission gear 26 as explained above, mounts the operatively connected driving assembly 16 and the actuator 18 into the injector 50, as an independent module. When mounted to the injector 50, the second mount 14 is vertically supported within the injector housing 52 by the cantilevered mounting arm 12a, without additional underlying support from the housing 52. Advantageously, therefore, the suspended actuator 18 is connected directly to the driving assembly 16, separate from connections to the injector housing 52. Thus, vibration of the actuator 18 and associated noise is dampened by the cantilevered mounting arm 12a and the first mount 12 before reaching the injector housing 52 and/or the external environment. That is, the cantilevered mounting arm 12a absorbs and suppresses vibration (and, therefore, associated noise) therethrough and at the fulcrum thereof, prior to reaching the injector housing 52.

Figure 4:
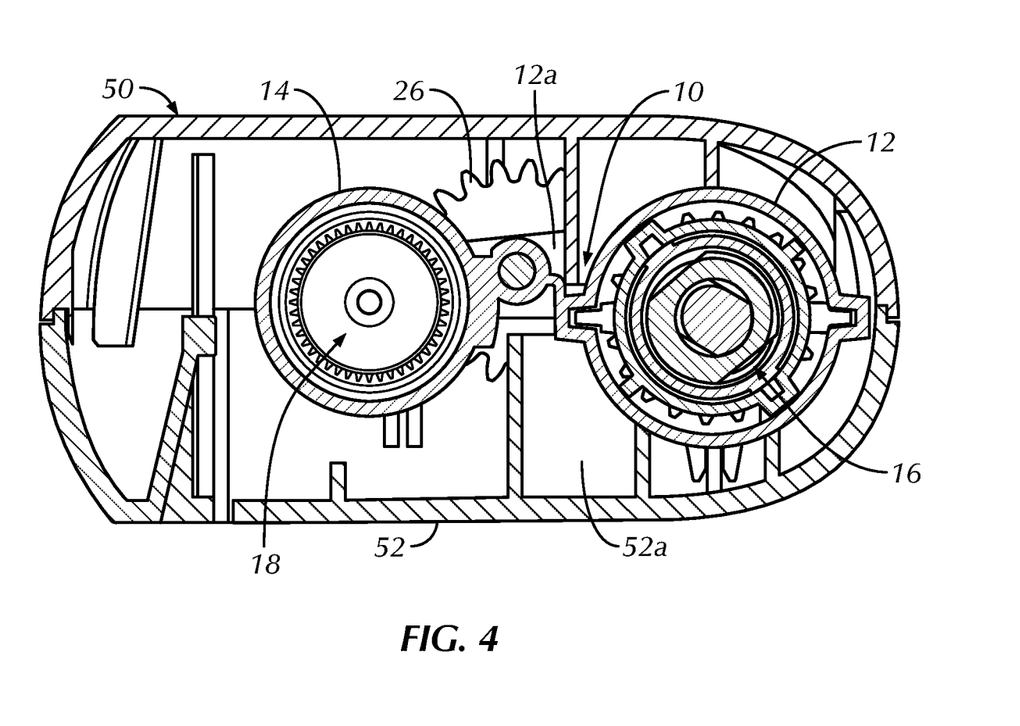
FIG. 4 is a cross-sectional view of the wearable injector of FIG. 1, taken along the sectional line 4-4 of FIG. 1, with the mounting module secured therein.
Figure 5:
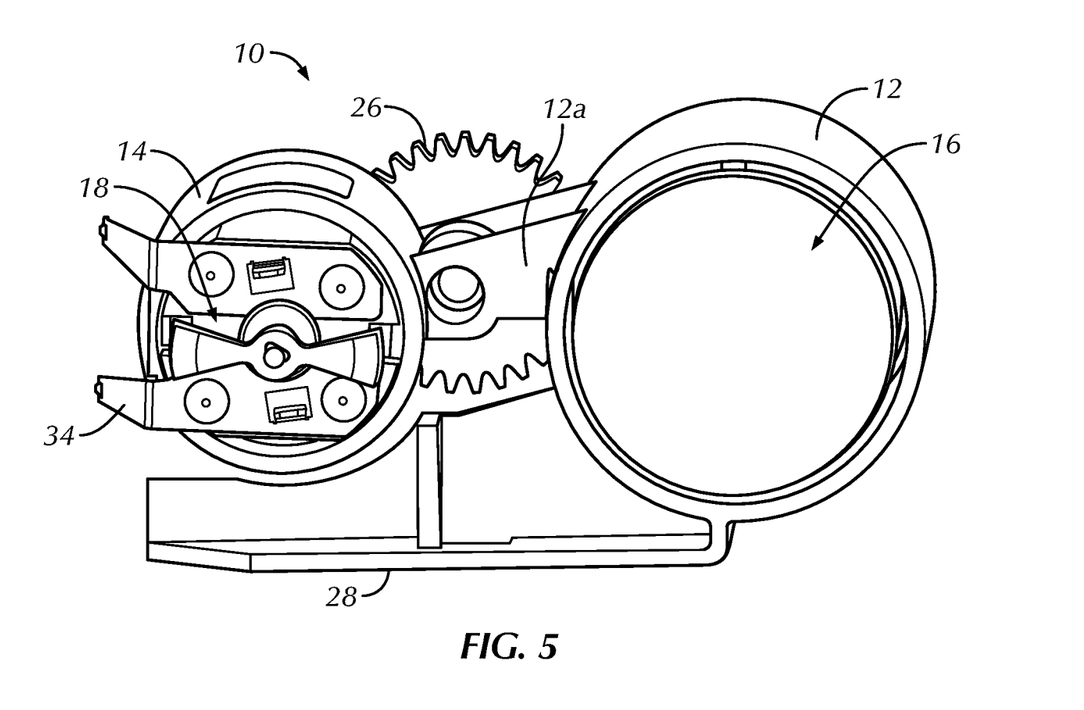
FIG. 5 is a top and front perspective view of the mounting module of FIG. 1, with an alternative mounting configuration for mounting to an injector.
Figure 7:
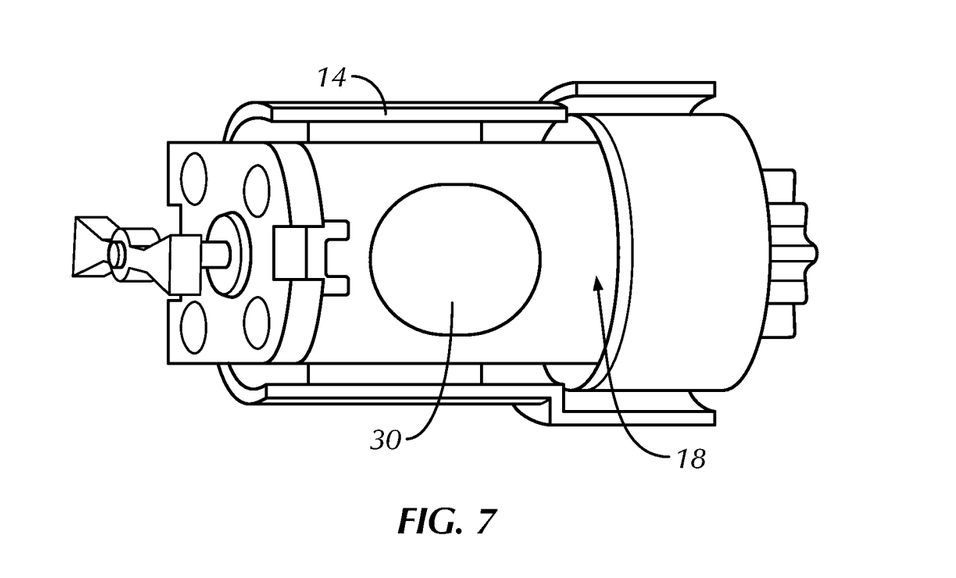
FIG. 7 is a partial cross-sectional view of the mounting module of FIG. 1, taken along the sectional line 7-7 of FIG. 1, with vibration reducing pads employed between the actuator and the corresponding mount of the mounting module.

As shown best in FIGS. 4 and 5, the mounting module 10 is independently, selectively, securable to the injector housing 52. In one embodiment, as shown in FIG. 4, the first mount 12 is selectively, removably securable to the injector housing 52. In the illustrated embodiment of FIG. 4, the housing 52 includes a cradle structure 52a to generally matingly receive and secure the first mount 12 thereupon (or therein), but the disclosure is not so limited. The housing 52 may, alternatively, removably, securely receive the mounting module 10 via any of numerous different means currently known or that later become known. For example, as alternatively shown in FIG. 5, the mounting module 10 may include a mounting plate 28 configured to selectively, removably secure the mounting module 10 to the injector housing 52. As one non-limiting example, the mounting plate 28 may snap into the injector housing 52. The mounting plate 28 may elastically, flexibly extend from the first mount 12. That is, similarly to the cantilevered mounting arm 12a, the mounting plate 28 may define a fulcrum at the interface between the mounting plate 28 and the first mount 12. Accordingly, the mounting plate 28 may further absorb and dampen vibration and associated noise prior to reaching the injector housing 52 and/or the external environment. Yet further alternatively, the mounting module 10 may be permanently, i.e., non-removably, secured to the housing 52, such as, for example, without limitation, via welding or bonding. Optionally, and as shown in FIG. 7, at least one vibration reducing pad 30 may be mounted between the actuator 18 and the second mount 14 to further absorb and dampen vibration prior to reaching the injector housing 52 and/or the external environment.

As shown in FIG. 1, a conventional power source 32, e.g., a battery, is mounted in the injector housing 52 to power the actuator 18. In one embodiment, a flexible electrical contact 34 is employed to connect the actuator 18 with the power source 32, whereby malleability of the flexible electrical contact 34 contributes to absorbing vibration of the actuator 18 to further minimize any transfer of vibration to the injector housing 52.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure, as set forth in the appended claims.

We claim:

1. An injector comprising:
   an injector housing configured to receive a cartridge therein;
   an injection needle fluidly connectable with the cartridge and configured to pierce a skin surface of a subject;
   an independent mounting module receivable within the injector housing, the mounting module comprising:
      a first mount selectively securable to the injector housing and the first mount having a cantilevered mounting arm extending therefrom; and
      a second mount attached to the cantilevered mounting arm and suspended therefrom, thereby being supported by the cantilevered mounting arm;
      a driving assembly mounted in and supported by the first mount, the driving assembly being engageable with the cartridge to expel a substance therefrom and through the injection needle;
      an actuator mounted in the second mount, the actuator being operatively connected with the driving assembly; and
   a battery mounted in the injector housing and connected to the actuator via a flexible electrical contact to power the actuator, whereby malleability of the flexible electrical contact contributes to absorbing vibration of the actuator.

2. The injector of claim 1, further comprising a transmission gear connecting the actuator with the driving assembly.

3. The injector of claim 2, wherein the cantilevered mounting arm is also configured to receive the transmission gear.

4. The injector of claim 1, wherein the first mount comprises a sleeve slidably receiving the driving assembly.

5. The injector of claim 1, wherein the second mount comprises a sleeve slidably receiving the actuator.

6. The injector of claim 1, wherein the actuator is a motor.

7. The injector of claim 1, further comprising at least one vibration reducing pad mounted between the actuator and the second mount.

8. The injector of claim 1, further comprising a mounting plate configured to selectively, secure the independent mounting module to the injector housing.

9. The injector of claim 8, wherein the mounting plate flexibly extends from the first mount.

10. The injector of claim 8, wherein the mounting plate is selectively, removably securable to the injector housing.

11. The injector of claim 1, wherein the first mount is selectively, removably securable to the injector housing.

12. An injector comprising:
   an injector housing configured to receive a cartridge therein;
   an injection needle fluidly connectable with the cartridge and configured to pierce a skin surface of a subject;
   an independent mounting module receivable within the injector housing, the mounting module comprising:
      a first mount, selectively securable within the injector housing, and having a cantilevered mounting arm extending therefrom; and
      a second mount attached to the cantilevered mounting arm and suspended therefrom, thereby being supported within the injector housing by the cantilevered mounting arm without additional underlying support from the housing;
      a driving assembly mounted in and supported by the first mount, the driving assembly being engageable with the cartridge to expel a substance therefrom and through the injection needle; and
      an actuator mounted in the second mount, the actuator being operatively connected with the driving assembly.

13. The injector of claim 12, wherein the independent mounting module further comprises a transmission gear connecting the actuator with the driving assembly.

14. The injector of claim 12, wherein the first mount comprises a sleeve slidably receiving the driving assembly.

15. The injector of claim 12, wherein the second mount comprises a sleeve slidably receiving the actuator.

16. The injector of claim 12, wherein the injector includes a cradle structure configured to receive the first mount.

17. The injector of claim 12, further comprising at least one vibration reducing pad mounted between the actuator and the second mount.

18. The injector of claim 12, further comprising a power source, and wherein the actuator is connected to the power source via a flexible electrical contact.

19. An injector comprising:
   an injector housing configured to receive a cartridge therein;
   an injection needle fluidly connectable with the cartridge and configured to pierce a skin surface of a subject;
   an independent mounting module receivable within the injector housing, the mounting module comprising:
      a first mount, selectively securable within the injector housing, and having a cantilevered mounting arm extending therefrom; and
      a second mount attached to the cantilevered mounting arm and suspended therefrom, thereby being supported within the injector housing by the cantilevered mounting arm without additional underlying support from the housing, thereby dampening transmission of vibration to the injector housing;

a driving assembly mounted in and supported by the first mount, the driving assembly being engageable with the cartridge to expel a substance therefrom and through the injection needle;

an actuator mounted in the second mount; and a transmission gear mounted to the mounting module and connecting the actuator with the driving assembly.

20. The injector of claim 19, wherein the injection needle is at least partially positioned within the injector housing.

\* \* \* \* \*